(12) United States Patent
Bosma et al.

(10) Patent No.: US 11,464,702 B2
(45) Date of Patent: Oct. 11, 2022

(54) THERMAL SKIN TREATMENT DEVICE

(71) Applicant: KONINKLIJKE PHILIPS N.V., Eindhoven (NL)

(72) Inventors: Ivar Bosma, Eindhoven (NL); Jeroen De Graaf, Eindhoven (NL); Bernardo Arnoldus Mulder, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 644 days.

(21) Appl. No.: 16/317,089

(22) PCT Filed: Aug. 2, 2017

(86) PCT No.: PCT/EP2017/069486
§ 371 (c)(1),
(2) Date: Jan. 11, 2019

(87) PCT Pub. No.: WO2018/024753
PCT Pub. Date: Feb. 8, 2018

(65) Prior Publication Data
US 2019/0290531 A1    Sep. 26, 2019

(30) Foreign Application Priority Data

Aug. 5, 2016 (EP) .................................. 16183132

(51) Int. Cl.
*A61H 7/00* (2006.01)
*A61F 7/00* (2006.01)
*A61F 7/02* (2006.01)

(52) U.S. Cl.
CPC ............... *A61H 7/00* (2013.01); *A61F 7/007* (2013.01); *A61F 2007/0004* (2013.01);
(Continued)

(58) Field of Classification Search
CPC .............. A61H 7/00; A61H 2201/0285; A61H 2201/5007; A61H 2201/5038;
(Continued)

(56) References Cited

U.S. PATENT DOCUMENTS 4,291,685 A * 9/1981 Taelman ................ A45D 40/26
219/227
4,585,002 A * 4/1986 Kissin ...................... A61F 5/00
607/96

(Continued)

FOREIGN PATENT DOCUMENTS

CN      202184905 U     4/2012
CN      203710229 U     7/2014
(Continued)

OTHER PUBLICATIONS

"IP landscape report treatment of eye bags and dark circles", author Marc Wolfs, IP&S.
"AST 235S 151173—RD Spoon—Temperature settings Hot Cold for Eye Energizer", Author Linda Keijzer, FDS.

*Primary Examiner* — Joseph D. Boecker
*Assistant Examiner* — Thomas W Greig

(57) ABSTRACT

The invention relates to a thermal skin treatment device comprising a skin contact component with a skin contact surface; a thermal energy component in thermal contact with the skin contact component; a temperature control circuit electrically connected to the thermal energy component and comprising a user interface; and an energy source electrically connected to said thermal energy component for energy supply. Said temperature control circuit is adapted to control an amount of energy supplied from said energy source to said thermal energy component such that a first predetermined temperature is maintained at the skin contact surface for a first duration, or a second predetermined temperature is maintained at the skin contact surface for a second duration, wherein said first predetermined tempera-
(Continued)

ture is in a range of 40° C.+/−2° C., and wherein said second predetermined temperature is in a range of 19° C.+/−2° C. The temperature control circuit is adapted to maintain for a predetermined duration, during operation, only said first predetermined temperature or said second predetermined temperature at the skin contact surface. The invention further relates to a method for non-therapeutic treatment of a human eye region by means of a thermal skin treatment device according to the invention.

20 Claims, 4 Drawing Sheets

(52) U.S. Cl.
CPC ......... *A61F 2007/0075* (2013.01); *A61F 2007/0078* (2013.01); *A61F 2007/0086* (2013.01); *A61F 2007/0087* (2013.01); *A61F 2007/0093* (2013.01); *A61F 2007/0095* (2013.01); *A61F 2007/0295* (2013.01); *A61F 2007/0296* (2013.01); *A61H 2201/0285* (2013.01); *A61H 2201/1253* (2013.01); *A61H 2201/5007* (2013.01); *A61H 2201/5038* (2013.01); *A61H 2201/5082* (2013.01); *A61H 2205/024* (2013.01); *A61H 2230/505* (2013.01); *A61H 2230/655* (2013.01)

(58) Field of Classification Search
CPC ...... A61H 2201/5082; A61H 2205/024; A61H 2230/505; A61H 2230/655; A61F 7/007; A61F 2007/0004; A61F 2007/0075; A61F 2007/0078; A61F 2007/0086; A61F 2007/0087; A61F 2007/0093; A61F 2007/0095; A61F 2007/0295; A61F 2007/0296; A61F 7/00; A61F 2007/0071–0076
See application file for complete search history.

(56) References Cited

U.S. PATENT DOCUMENTS

| | | | | |
|---|---|---|---|---|
| 5,209,227 | A * | 5/1993 | Deutsch | A61M 35/003 607/104 |
| 5,551,949 | A * | 9/1996 | Kim | A61H 23/02 601/15 |
| 6,001,070 | A | 12/1999 | Gebhard | |
| 7,223,250 | B2 * | 5/2007 | Brattesani | A61H 23/02 601/46 |
| 2008/0300529 | A1 * | 12/2008 | Reinstein | A61F 7/007 604/20 |
| 2011/0202048 | A1 * | 8/2011 | Nebrigic | A61F 7/007 606/22 |
| 2012/0035475 | A1 * | 2/2012 | Barthe | A61B 8/4209 600/439 |
| 2012/0065556 | A1 * | 3/2012 | Smith | A61F 7/007 601/89 |
| 2013/0137940 | A1 * | 5/2013 | Schafer | A61B 10/0012 600/301 |
| 2014/0200487 | A1 | 7/2014 | Ramdas | |
| 2015/0065909 | A1 * | 3/2015 | Wajima | A61F 7/007 600/555 |
| 2015/0121900 | A1 * | 5/2015 | Yamazaki | F25B 21/04 62/3.3 |
| 2017/0128258 | A1 * | 5/2017 | Diller | A61F 7/007 |
| 2019/0290531 | A1 | 9/2019 | Bosma | |

FOREIGN PATENT DOCUMENTS

| | | |
|---|---|---|
| CN | 203970890 U | 12/2014 |
| CN | 205108300 U | 3/2016 |
| CN | 105816268 A | 8/2016 |
| EP | 0330472 A2 | 8/1989 |
| JP | 2015150033 A | 8/2015 |
| WO | 2008151260 A2 | 12/2008 |
| WO | 2015071810 A1 | 5/2015 |
| WO | 2016004295 A1 | 1/2016 |

* cited by examiner

THERMAL SKIN TREATMENT DEVICE

This application is the U.S. National Phase application under 35 U.S.C. § 371 of International Application No. PCT/EP2017/069486, filed on Aug. 2, 2017, which claims the benefit of International Application No. 16183132.6 filed on Aug. 5, 2016. These applications are hereby incorporated by reference herein.

FIELD OF THE INVENTION

The invention relates to a thermal skin treatment device, in particular for treating the human eye region, comprising a skin contact component with a skin contact surface, a thermal energy component in thermal contact with the skin contact component, a temperature control circuit electrically connected to the thermal energy component, said temperature control circuit comprising a user interface, and an energy source electrically connected to said thermal energy component for energy supply.

The invention further relates to a method for non-therapeutic treatment of a human eye region by means of a thermal skin treatment device.

BACKGROUND OF THE INVENTION

U.S. Pat. No. 4,291,685 discloses a cosmetic device for applying heat and substances to the face or other parts of the human body. The device comprises a spoon-shaped hollow skin contact component, which is used to simultaneously apply heat and vibration to the skin. The device is intended to provide an ironing function, wherein the user may manually adjust the temperatures applied to the skin. Generally, the mere application of heat and vibration simultaneously may serve to intensify the application of substances, but does not show to have a positive effect on the skin per se, since, according to this prior art, the temperature applied by the user is not selected specifically for such positive effect.

U.S. Pat. No. 6,001,070 discloses a similar device for applying a combination of heat and massage. The temperature of the spoon-shaped surface of the skin contact component is thermostatically controlled to be in a range of 36.7° C. (98° F.) to 48.9° C. (120° F.), in particular in a range of 42.2° C. (108° F.) to 44.4° C. (112° F.). Whereas such application of a combination of heat and massage may provide a convenient feeling to the user, the success of such a treatment with regard to objective medical or cosmetic effects on the face of the user is rather small. In particular, adverse effects may occur due to the temperature being in a range including temperatures which were found to produce skin alterations, aging effects and even injuries to the skin. The treatment is not limited to specific durations, so that such adverse effects may occur due to a treatment being too long. Still further, it has been shown that the temperature control of the skin contacting surface cannot be guaranteed with the setup of these prior art devices, and temperature peaks outside the predetermined range or outside the temperature selected by the user may occur.

WO 2008/151260 A2 discloses a skin care kit using a Peltier thermoelectric element. According to this prior art, a heating or cooling treatment is applied to the skin or a body part to be treated with the thermoelectric Peltier element by selecting a corresponding polarity of the voltage supplied to the Peltier element and, if necessary, changing the polarity. A plurality of treatment durations, including a large number of values between 1 second and 60 minutes, and a plurality of chemical compositions to be applied to the skin in the course of the treatment, are disclosed in this document. Further, two different lists, each comprising a large number of temperature values respectively ranging from −6.7° C. (20° F.) to 37.2° C. (99° F.) and from 4.4° C. (40° F.) to about 43.3° C. (110° F.), and each including multiple intermediate values, are disclosed in this prior art. Most of the treatment durations and temperature values defined in this document were found not to provide any positive effect, on the contrary, they may produce adverse effects when combined with each other to treat the skin. Further, it is not clear which duration, temperature and composition are to be applied in combination to effectively treat the skin to reach any specific positive result. Still further, a precise temperature control to maintain the desired specific temperature level throughout the duration of the treatment cannot be reached with the setup of the device disclosed in this prior art.

WO 2016/004295 A1 discloses devices and methods to conduct cryotherapy with both an enhanced healing process and a reduced risk of collateral ischemic injury. With the disclosed devices and methods long term ischemia during cryotherapy of extended duration may be achieved by an intermittent raising of the tissue temperature to transiently increase perfusion. For this purpose it is desirable to alternate the skin temperature between lower (15° C.-20° C.) cooling values and higher (37° C.-42° C.) warming values. Cooling lowers blood perfusion for reduced tissue swelling, lowers nerve conduction velocity for reduced pain sensation, and reduces inflammation processes. Heating elevates blood flow and metabolic rates to avoid long term ischemia and the potential for tissue injury, prevents subsequent ischemic reperfusion injury, and improves rates of tissue recovery.

Generally, whereas a couple of different skin treatment devices are known from the prior art, these devices have shown to be not well-suited for a specific treatment of the human eye region to reduce eye fatigue, puffiness and the appearance of dark circles in the eye region.

SUMMARY OF THE INVENTION

It is an object of the invention to provide a thermal skin treatment device, which is particularly suited to treat the human eye region in order to reduce puffiness, eye fatigue and dark circles.

According to the invention, this object is achieved with a thermal skin treatment device, comprising a skin contact component with a skin contact surface, a thermal energy component in thermal contact with the skin contact component, a temperature control circuit electrically connected to the thermal energy component, said temperature control circuit comprising a user interface, an energy source electrically connected to said thermal energy component for energy supply, wherein said temperature control circuit is adapted to control an amount of energy supplied from said energy source to said thermal energy component such that a first predetermined temperature is maintained at the skin contact surface for a first duration, or a second predetermined temperature is maintained at the skin contact surface for a second duration, wherein said first predetermined temperature is in a range of 40° C.+/−2° C., and wherein said second predetermined temperature is in a range of 19° C.+/−2° C., and wherein said temperature control circuit is adapted to maintain for a predetermined duration, during operation, only said first predetermined temperature or said second predetermined temperature at the skin contact surface.

The thermal skin treatment device according to the invention is adapted to control the temperature level of the skin contact surface of the skin contact component at one of two specific temperature levels, including a range of +/−2° C. below or above said specific temperature levels. The first temperature range is 40° C.+/−2° C., i.e. a range from 38° C. to 42° C. This range, which is only slightly above normal human body temperature, was found to be the optimum temperature range for treating eye fatigue. The second temperature range is 19° C.+/−2° C., i.e. a range from 17° C. to 21° C. This range is 17.5° C.+/−2° C. below the normal human body temperature of 36.5° C. This second temperature range was found to effectively reduce eye puffiness. Further, the first and second temperature ranges may efficiently reduce dark circles around the eye if an alternating treatment is applied wherein the first temperature and the second temperature are applied one after the other.

According to the invention, the temperature control circuit is adapted to maintain for a predetermined duration, during operation, only said first predetermined temperature or said second predetermined temperature at the skin contact surface. Thus, it is ensured that, during operation, only said first predetermined temperature within said range of 40° C.+/−2° C. or said second predetermined temperature within said range of 19° C.+/−2° C. can be maintained at the skin contact surface for a predefined duration. This means that the temperature control circuit can maintain the temperature of the skin contact surface of the skin contact component, i.e. maintain the temperature for a predetermined duration, only at a value within each one of said two specific temperature ranges. This will effectively prevent normal operation of the device at temperature levels outside said two specific temperature ranges, and thus prevent skin damage or any other adverse effects resulting from the application of temperatures outside said two specific temperature ranges. The fact that the temperature control circuit can maintain the temperature of the skin contact surface of the skin contact component, for a predetermined duration, only at a value within each one of said two specific temperature ranges does not exclude that the skin contact surface can have a temperature outside said two specific temperature ranges, for example when the device is not operative or when the temperature of the skin contact surface is adjusted to a temperature within one of said two specific ranges. It is to be understood that, when the temperature of the skin contact surface is adjusted to a temperature within one of said two specific ranges, the temperature will usually gradually change, so that the temperature is not maintained at a particular value for a predetermined duration.

To generate the first or second predetermined temperature at the skin contact surface, a thermal energy component is incorporated in the thermal skin treatment device. The thermal energy component is in thermal contact with the skin contact component. The term "thermal contact" of two components is to be understood to mean that the two components are directly attached to each other to provide a direct heat flow across the mutual contact surfaces of the two components. The term "thermal contact" is further to be understood to be a contact interface having a gap filled with a thermally conductive liquid, paste or solid material. Preferably, in such a "thermal contact" no air gap is present between the two components.

As a result of said thermal contact, a direct heat flow from the thermal energy component to the skin contact component and vice versa is provided. The skin contact component may be manufactured from a material having a high effective heat capacity and a high thermal conductivity like, e.g. a metal.

It is to be understood that the thermal energy component may be composed of a single element or multiple elements. The thermal energy component may comprise a heating element and a cooling element separate from each other and both being connected to the temperature control circuit to provide the first and the second predetermined temperatures at the skin contact surface. The thermal energy component may alternatively comprise a single thermal energy element, which is adapted to both heat the skin contact surface and cool the heat contact surface. The thermal energy component may comprise a fan or cooling-liquid system to dissipate heat out of the thermal energy component when cooling the skin contact component.

A suitable example of such a single thermal energy element is a Peltier element. When the thermal energy component comprises or consists of a Peltier element, the skin treatment device preferably further comprises a heat sink in thermal contact with the Peltier element. The heat sink may be manufactured from a material having a high effective heat capacity and a high thermal conductivity like a metal. A Peltier element is able to act as a heat pump in two different directions, depending on the polarity of an electrical DC voltage supplied to the Peltier element. As a result, to cool the skin contact component, the Peltier element may pump heat out of the skin contact component and into the heat sink. To heat the skin contact component, the Peltier element may pump heat out of the heat sink and into the skin contact component. It is to be understood that a heat sink may also be incorporated in the thermal skin treatment device when the thermal skin treatment device comprises a type of thermal energy component different from a Peltier element.

The thermal energy component is preferably interposed between the skin contact component and the heat sink, such that the skin contact component is in thermal contact with the thermal energy component on one side of the thermal energy component and the heat sink is in thermal contact with the thermal energy component on an opposite side of the thermal energy component. The thermal energy component may act as a bi-directional heat pump, wherein, depending on the polarity of the DC-voltage provided by the energy source electrically connected to the thermal energy component, either heat is withdrawn from the skin contact component and transported by the thermal energy component to the heat sink to generate the second predetermined temperature at the skin contact surface, or heat is withdrawn from the heat sink and transported by the thermal energy component to the skin contact component to generate the first predetermined temperature at the skin contact surface.

A temperature control circuit is provided in the thermal skin treatment device according to the invention. The temperature control circuit is electrically connected to the thermal energy component to control the heat pumping action provided by the thermal energy component and thereby control the temperature at the skin contact surface of the skin contact component. It is to be understood that the energy source may be electrically connected to the thermal energy component via said temperature control circuit, such that the energy provided to the thermal energy component from said energy source may be controlled by the temperature control circuit with regard to the polarity of the DC voltage and the amount of energy supplied to the thermal energy component. The amount of energy supplied to the thermal energy component may be controlled in such a way that the energy supply is alternately turned on and off, wherein the duration of the ON-time periods and/or the duration of the OFF-time periods are controlled. Further, or alternatively, a level of the electric voltage and/or the electric current provided to the thermal energy component may for example be controlled.

The temperature control circuit further comprises a user interface which may be adapted to receive input from a user and to output information to the user. The user interface could e.g. be embodied as a touch-sensitive display, as a single or multiple pushbuttons, as a single or multiple LEDs, or the like. It is to be understood that the user interface may further comprise, or be embodied as, a wireless connection or cable connection to an electronic device, like a base station, a smartphone, a computer, or the like. Programming functions, information about the status of the thermal skin treatment device, and visual or acoustic signals may be provided via said electronic device. The temperature control circuit may further comprise logic electronic components, like programmable components to control specific treatment routines involving the first and/or the second predetermined temperature and/or the first and second durations, and electronic memory components to store parameters and firmware settings. In particular, specific sequences of application of the two predetermined temperatures and durations may be stored in the temperature control circuit and controlled by the temperature control circuit. For example, multiple different selectable durations for maintaining the first and the second predetermined temperatures according to different treatment modes may be predetermined and stored in the temperature control circuit.

The energy source may be realized by different embodiments. For example, an energy interface like a plug or socket may be incorporated to connect the thermal skin treatment device to a source of energy, like an external transformer coupled to the public energy supply network. The energy source may alternatively be embodied as a battery component, wherein exchangeable batteries may be positioned in a battery compartment or a rechargeable battery may be employed as the energy source. In such embodiments, preferably an electrical interface is provided to recharge the battery when placed in the thermal skin treatment device.

According to the invention, a thermal skin treatment device is provided, which is able to generate one out of two predetermined specific temperatures at a skin contact surface. It was found that the range of 40° C.+/−2° C., on the one hand, and the range of 19° C.+/−2° C., on the other hand, are specifically adapted and effective for treatment of the human eye region. Although temperatures below the second predetermined temperature or temperatures above the first predetermined temperature generally impart a stronger thermal effect on the skin of the user, research undertaken by the inventors showed that such lower and higher temperatures are rather inconvenient to the user. Such temperatures below and above the prescribed ranges of, respectively, 19° C.+/−2° C. and 40° C.+/−2° C. might cause skin damage and may even actually increase skin aging, thus causing detrimental effects. Further, it was found that, if a higher temperature than the first predetermined temperature or a lower temperature than the second predetermined temperature is applied, a specific effect such as reducing eye puffiness, eye fatigue or dark circles is not achieved at all, or not as effectively as by applying the prescribed first and/or second predetermined temperature. In research studies conducted by the inventors, the first and second predetermined temperatures were found to be both most effective at reducing eye puffiness, eye fatigue or dark circles and convenient to a user when applied to the eye regions.

According to a first preferred embodiment of the invention, said user interface is adapted for selection between at least two different operating modes selected from a first operating mode, wherein the first predetermined temperature is maintained at the skin contact surface and the first duration is in a range from 60 to 240 seconds, a second operating mode, wherein the second predetermined temperature is maintained at the skin contact surface and the second duration is in a range from 30 to 90 seconds, and a third operating mode, wherein alternately the first predetermined temperature is maintained at the skin contact surface, with the first duration being in a range from 60 to 150 seconds, and the second predetermined temperature is maintained at the skin contact surface, with the second duration being in a range from of 5 to 30 seconds. Each of these operating modes, when selected, is to be applied in a single treatment for a single eye region, and may be repeated thereafter for the treatment of the other eye region.

According to this preferred embodiment, two, three or more different operating modes corresponding to different treatment programs can be selected and applied by the thermal skin treatment device. These treatment programs all include treatments at the first or the second predetermined temperature, which allows to calibrate exactly the temperature control circuit to maintain these temperatures with high precision in all three operating modes.

The first operation mode provides a relaxing effect and diminishes eye fatigue by a warm treatment at the first predetermined temperature for a predetermined duration selected within the range from 60 to 240 seconds. It is to be understood that a predetermined duration may be stored within the thermal skin treatment device, and will thus be applied if the user selects the first operation mode. The user may further select a specific duration within the range from 60 to 240 seconds depending on the user's specific needs, or the user may program the device with an individual duration within said range, which is then repeatedly applied when the first operation mode is selected.

The second operation mode was found to be most effective at reducing eye puffiness and refreshing the eye by a cold treatment. Again, the duration may be preprogrammed, selected by the user, or programmed by the user within the range from 30 to 90 seconds.

In the third operation mode, the first predetermined temperature is maintained for a first duration to stimulate blood flow and trigger fresh oxygen and nutrient delivery to the eye and to the eye region by a warm treatment. Hereafter, the second predetermined temperature is applied for a second duration in the range from 5 to 30 seconds. This produces a final refreshing touch, constricts the blood vessels again, and thus causes dark circles to be less visible.

Generally, it is to be understood that the temperature control circuit is adapted to maintain the selected temperature at a constant level. In a preferred embodiment of the invention, however, the temperature control circuit is adapted to control the amount of energy supplied from said energy source to said thermal energy component such that the first predetermined temperature periodically fluctuates within said range of 40° C.+/−2° C. and/or the second predetermined temperature periodically fluctuates within said range of 19° C.+/−2° C. In this embodiment, the temperature control circuit is adapted to alternatively or additionally control the first predetermined temperature and/or the second predetermined temperature in a fluctuating mode, wherein the temperature periodically fluctuates around a selected temperature within a small range of e.g. 1° C. or 2° C. to generate an undulating temperature curve over time. In this fluctuating mode, the temperature thus periodically changes from e.g. 39° C. to 40° C. and vice versa. This may preferably be done with a frequency of 1-5 changes per minute. The fluctuating mode produces an improved subjective feeling to the user and has been found to intensify the treatment effects.

According to a further preferred embodiment of the invention, said temperature control circuit is adapted to receive a user input via said user interface, said user input representing a selection of a duration by a user, wherein said temperature control circuit is adapted to control said first duration depending on the user input and/or to control said second duration depending on the user input. According to this embodiment, the user may select a preferred value of the first duration and/or the second duration, or a parameter related to the first and/or the second duration, during which the first and/or the second predetermined temperatures are to be maintained. The duration may preferably be selected from the range of durations for the first predetermined temperature, the second predetermined temperature or for the sequence of alternately applying the first predetermined temperature and the second predetermined temperature as described hereinbefore. Alternatively, a parameter like "quick treatment" or "intensive treatment" may be selected to respectively shorten or extend the first and/or the second duration within predetermined ranges.

According to a further preferred embodiment of the invention, said user interface is adapted for selection of a thermal massage operating mode, wherein, in a first phase, the skin contact surface is maintained at the first predetermined temperature, wherein the first duration is from 60 to 150 seconds; in a second phase after the first phase, the skin contact surface is maintained at the second predetermined temperature, wherein the second duration is from 5 to 30 seconds; and in an intermediate phase, starting after the first phase has ended and before the second phase has started, the user is instructed to apply a massage to the skin for a duration from 15 to 60 seconds.

With this embodiment, a thermal massage operating mode is provided. It is to be understood that this thermal massage operating mode may be a specific example of the third operating mode described herebefore. Alternatively, the thermal massage operating mode may be an additional fourth operating mode, which can be selected by the user. In this thermal massage operating mode, a massage phase is interposed between the first phase of applying the first predetermined temperature and the second phase of applying the second predetermined temperature. The massage phase may be signalized to the user by a visual or acoustic signal, e.g. in that the beginning and the end of the massage phase are signalized by such a signal such that the user may apply a passive or manual massage during the massage phase without any actuated action by the thermal skin treatment device. The massage phase may alternatively involve applying a vibration or another mechanical action by the thermal skin treatment device to apply an active massage to the skin of the user. It was found that, in particular when treating the eyes of a user, such active massage may cause damage or injury to the eye or an uncomfortable feeling. Therefore, a passive massage manually applied by means of a passive soft surface structure provided on the skin treatment device is preferred for eye treatment.

According to a further preferred embodiment of the invention, at least one of the first and second durations is programmable via the user interface. According to this embodiment, the user may select or program a preferred value for the first and/or the second duration. The selected duration will be stored in the temperature control circuit and thus will be applied for any following treatment. Alternatively, the selected duration can be selected as a preprogrammed treatment procedure. In particular, a plurality of preprogrammed treatment procedures may be programmed by the user and stored within the temperature control circuit, such that the user may select from said plurality of preprogrammed treatment procedures.

In a further preferred embodiment of the invention, the temperature control circuit is adapted to receive a user input via said user interface, said user input representing a temperature selection of a user, wherein said temperature control unit is adapted to adjust said first predetermined temperature, within the range of 40° C.+/−2° C., to a higher or a lower value depending on the user input and/or to adjust said second predetermined temperature, within the range of 19° C.+/−2° C., to a higher or a lower value depending on the user input. According to this embodiment, the user may define the temperature within the range of the first predetermined temperature or within the range of the second predetermined temperature such that the defined temperature is maintained, e.g. at the upper limit of said range or at the lower limit of said range, for respectively the first or second duration.

According to a further preferred embodiment of the invention, the thermal skin treatment device further comprises a temperature sensor coupled to the temperature control circuit for transmission of a temperature signal corresponding to a temperature detected by the temperature sensor, wherein said temperature sensor is in thermal contact with the skin contact component.

Such a temperature sensor in thermal contact with the skin contact component may allow accurate detection of the temperature of the skin contact component, and thus may produce reliable data representing the temperature of the skin contact surface of the skin contact component. Direct thermal contact between the temperature sensor and the skin contact component, i.e. a direct heat transfer path from the skin contact component into the temperature sensor without the presence an air gap, allows for a measurement of the temperature without any substantial time delay or temperature shift, and thus is well-suited for accurate real-time control of the temperature of the skin contact surface. The temperature sensor may be embodied as a thermocouple or an NTC resistor. The temperature sensor may be directly attached to the skin contact component with a suitable heat transfer paste or material interposed. It is preferred to arrange the temperature sensor within an aperture, a recess or an opening within the skin contact component and to position the temperature sensor at a distance from the area of thermal contact between the thermal energy component and the skin contact component to prevent local measurement errors induced by the thermal energy component.

In a particularly preferred embodiment of the invention, the temperature control circuit is adapted to control the amount of energy supplied from the energy source to the thermal energy component depending on the temperature signal transmitted by the temperature sensor. According to this preferred embodiment, the temperature sensor is integrated into a closed-loop control system of the temperature control circuit, such that the amount and/or the polarity of the energy supplied to the thermal energy component, which might be embodied as a Peltier element, is controlled depending on the temperature measured by the temperature sensor. This allows for a quick response time of the temperature control circuit. The inventors have found that, while some types of thermal energy components like e.g. a Peltier element generally show a quick response as regards their heating effect, cooling effect and/or heat pumping effect, the skin contact surface nevertheless often experiences peak temperature values outside the desired temperature ranges due to changes occurring in the size of the part of the skin contact surface which actually is in contact with the skin of the user. Such changes e.g. occur when the user initially brings the device into contact with the skin, or when the user slightly moves the device while the latter is in contact with the skin. Thus, to avoid inconvenience or even injuries to the skin of the user as a result of temperatures outside the desired temperature ranges, a quick and reliable temperature control is required. For this reason, a closed-loop control is preferred, wherein the temperature sensor signal represents the temperature of the skin contact component in real time without any substantial delay. As a result, significant temperature peaks outside the desired temperature ranges, both in an upward and in a downward direction, can be reliably avoided, even when sudden changes of the heat flow across the skin contact surface occur, for example when the user brings the skin contact surface into contact with the skin.

According to a further preferred embodiment of the invention, the thermal skin treatment device further comprises a heat sink in thermal contact with the thermal energy component, wherein a ratio of a heat capacity of the skin contact component to a heat capacity of the heat sink is in a range from 1:2 to 1:10, preferably in a range from 1:2.5 to 1:5. Generally, the heat capacity of the heat sink should preferably be adapted to the level of the first and second predetermined temperatures and the first and second durations for applying the first and second predetermined temperature, such that the heat sink is heated and cooled to a reasonable temperature level. Thus, a lower limit of the heat capacity of the heat sink is required to prevent the temperature of the heat sink becoming too high. When the heat sink temperature is too high, heat may flow back from the heat sink to the skin contact component after switching off the device, and the skin contact surface may be heated to high temperatures, which may cause injuries.

When a treatment procedure with alternating temperatures is applied, the heat sink will be at a lower temperature after generation of the relatively high first predetermined temperature at the skin contact surface. This will increase the efficiency of the thermal energy component when the relatively low second predetermined temperature is subsequently applied at the skin contact surface. Thus, an increased upper limit of the heat capacity of the heat sink will improve the efficiency of the thermal energy component in such alternating treatment procedures.

The heat capacity of the skin contact component is generally considered to have two consequences. First, a high heat capacity of the skin contact component will provide a latency of the temperature changes of the skin contact component, and thus will inherently reduce temperature peaks which may occur as a result of changes of the size of the part of the skin contact surface actually in contact with the skin. Secondly, a small heat capacity of the skin contact component will produce a quick reaction time to heat transferred into the skin contact component by the thermal energy component, and thus will allow a precise and quick closed-loop control of the temperature of the skin contact component with short delay times. By adjusting the heat capacity of the skin contact component to a certain ratio in relation to the heat capacity of the heat sink, both the efficiency and the control response times are optimized to a preferred level and are well balanced. The heat capacity of the skin contact component and the heat sink depend on the specific heat capacities of the materials of the skin contact component and the heat sink as well as on the mass of the skin contact component and the heat sink.

In a further preferred embodiment of the invention, the skin contact surface has a concave shape. The curvature of the skin contact surface may have an average radius along said surface in a range from 50 mm to 200 mm, preferably in a range from 80 mm to 120 mm. When the skin contact surface has such a concave shape, the skin contact surface may be brought snuggly into contact with the eye lids of the user, with the lid being closed over the eye, such as to enable applying any treatment procedure to the eye lid, like refreshing, reducing eye puffiness or reducing dark circles. The skin contact component may be replaceable and the skin treatment device may comprise a plurality of different skin contact components, which can be alternatively attached to the thermal skin treatment device, wherein the different skin contact components may have different geometries of the skin contact surface such as to enable providing treatment not only to the eye lid, but to other skin regions of the face or the body of a user as well.

According to a further preferred embodiment of the invention, the skin contact surface is arranged at an end portion of the thermal skin treatment device, and a massage contact surface having a non-smooth surface is arranged at said end portion. According to this embodiment, a massage contact surface is incorporated in the thermal skin treatment device, such that the user may manually apply a passive massage to the treated skin area by means of the massage contact surface. The massage contact surface may comprise a specific material like a soft rubber material, and may have a structured surface area comprising, e.g., multiple elevations, buckles or the like in a spaced arrangement to each other. The massage contact surface may preferably be arranged at the same end portion of the thermal skin treatment device where the thermal contact surface is also arranged, but on an opposite side of the device, such that the user may simply rotate the thermal skin treatment device along its longitudinal axis to apply a massage after a thermal treatment and vice versa.

According to a further preferred embodiment, the user interface comprises signaling means for signaling to the user at least one parameter related to a temperature or a duration controlled by the temperature control circuit. Such signaling means may present to the user a signal related to the type of operating mode, like e.g. a visual signal, text information or the like. Further, the temperature may be signalized by a visual signal, like e.g. a blue colored signal for the relatively low second predetermined temperature and a red colored signal for the relatively high first predetermined temperature. Further, acoustic signals may be provided by the user interface, e.g. for signaling the beginning of a treatment or a treatment phase or for signaling the end of a treatment or a treatment phase. In particular, in operating modes wherein a passive massage is to be applied by the user between two thermal treatments, the end of the first thermal treatment and the beginning of the second thermal treatment shall preferably be signalized by such a signal and the user may thus clearly get a signal for starting and ending the passive massage.

According to a preferred embodiment of the invention, said skin contact component, said thermal energy component, said heat sink (if present), said temperature control circuit, said temperature sensor (if present), and said energy source are integrally mounted in a handheld device, said energy source being embodied as a rechargeable or replaceable battery. According to this embodiment, all components involved in the function of the thermal skin treatment device are integrated into one handheld device, e.g. in a cylindrical or frusto-conical housing, with the skin contact surface arranged at a tip or end portion of the housing to allow comfortable handling of the device by the user.

According to a further preferred embodiment of the invention, the thermal skin treatment device further comprises a skin sensor adapted to measure an electrical resistivity of the skin, an electrical capacity of the skin, a temperature of the skin and/or a humidity of the skin, wherein said skin sensor is coupled to said temperature control circuit for signal transmission, and wherein said temperature control circuit is adapted to display a skin condition on said user interface and/or to control said first or second predetermined temperature or said first or second duration depending on a signal transmitted by the skin sensor. Such a skin sensor may be integrated into a massage pad or into the skin contact surface and helps to individually adapt the treatment parameters, like temperatures and durations, to the skin condition of an individual user.

The invention further relates to a method for non-therapeutic treatment of a human eye region by means of a thermal skin treatment device, having a skin contact component with a skin contact surface, a thermal energy component in thermal contact with the skin contact component, a temperature control circuit electrically connected to the thermal energy component, said temperature control circuit comprising a user interface, and an energy source electrically connected to said thermal energy component for energy supply, the method comprising controlling, by means of said temperature control circuit, an amount of energy supplied from said energy source to said thermal energy component such that a first predetermined temperature is maintained at the skin contact surface for a first duration, or a second predetermined temperature is maintained at the skin contact surface for a second duration, wherein said first predetermined temperature is in a range of 40° C.+/−2° C., and wherein said second predetermined temperature is in a range of 19° C.+/−2° C., and maintaining for a predetermined duration, by means of said temperature control circuit, only said first predetermined temperature or said second predetermined temperature at the skin contact surface.

It is to be understood that a preferred embodiment of the present invention can also be any combination of the dependent claims, or a combination of the embodiments described hereinbefore, with the respective independent claim.

These and other aspects of the invention will be apparent from and elucidated with reference to the embodiments described hereinafter.

BRIEF DESCRIPTION OF THE DRAWINGS

A preferred embodiment of the thermal skin treatment device according to the invention is described with reference to the appending figures.

In the following drawings.

DETAILED DESCRIPTION OF THE EMBODIMENTS

Figure 1:
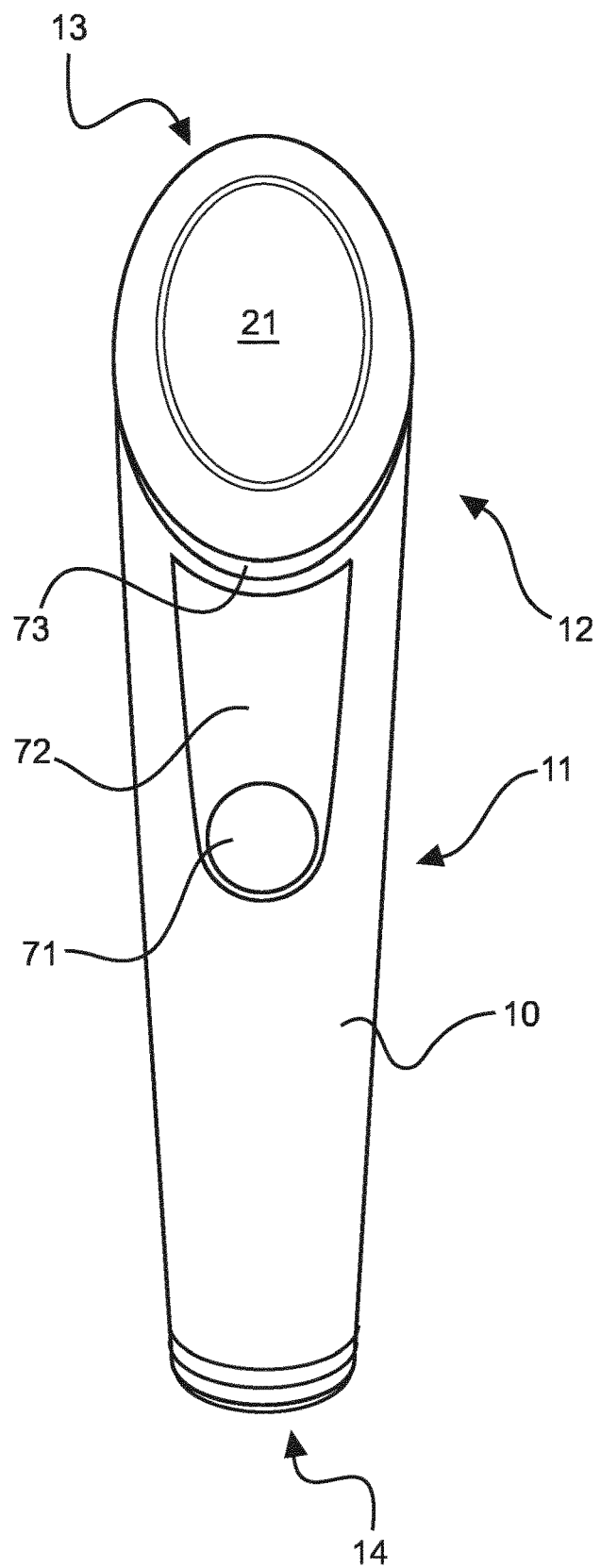
FIG. 1 shows a front view of a thermal skin treatment device according to the invention.
Figure 2:
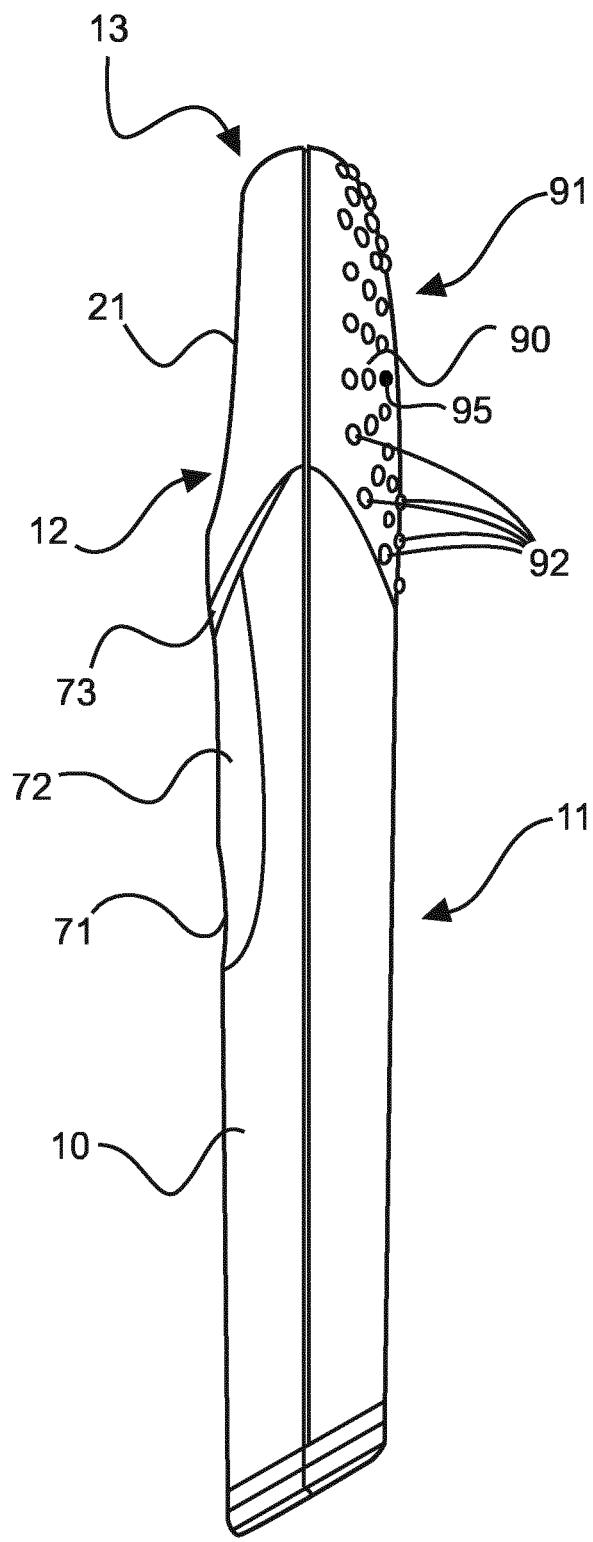
FIG. 2 shows a lateral view of the device according to FIG. 1.

The thermal skin treatment device according to the preferred embodiment comprises a housing 10, which is generally designed as a slim-shaped frusto-conical body with an upper section 12 and a lower section 11 reaching to a bottom end 14 of the housing. The lower section 11 has a shape suitable to act as a handle for being gripped by a user. The upper section 12 is functionally designed as a treatment head. The treatment head is arranged at an upper end portion 13 of the housing 10 and comprises, on a front side of the treatment head, a skin contact surface 21 having a concave shape. The skin contact surface 21 is formed on the outward-facing front side of a skin contact component 20. The skin contact component 20 is manufactured from a metal, e.g. aluminum.

Opposite to the skin contact surface 21 of the skin contact component 20, a Peltier element 30 is attached to the skin contact component 20 on the back side thereof. The Peltier element 30 is in direct contact with the skin contact component 20, and thus is in thermal contact with the skin contact component 20 for heat transmission between the skin contact component 20 and the Peltier element 30.

Figure 3:
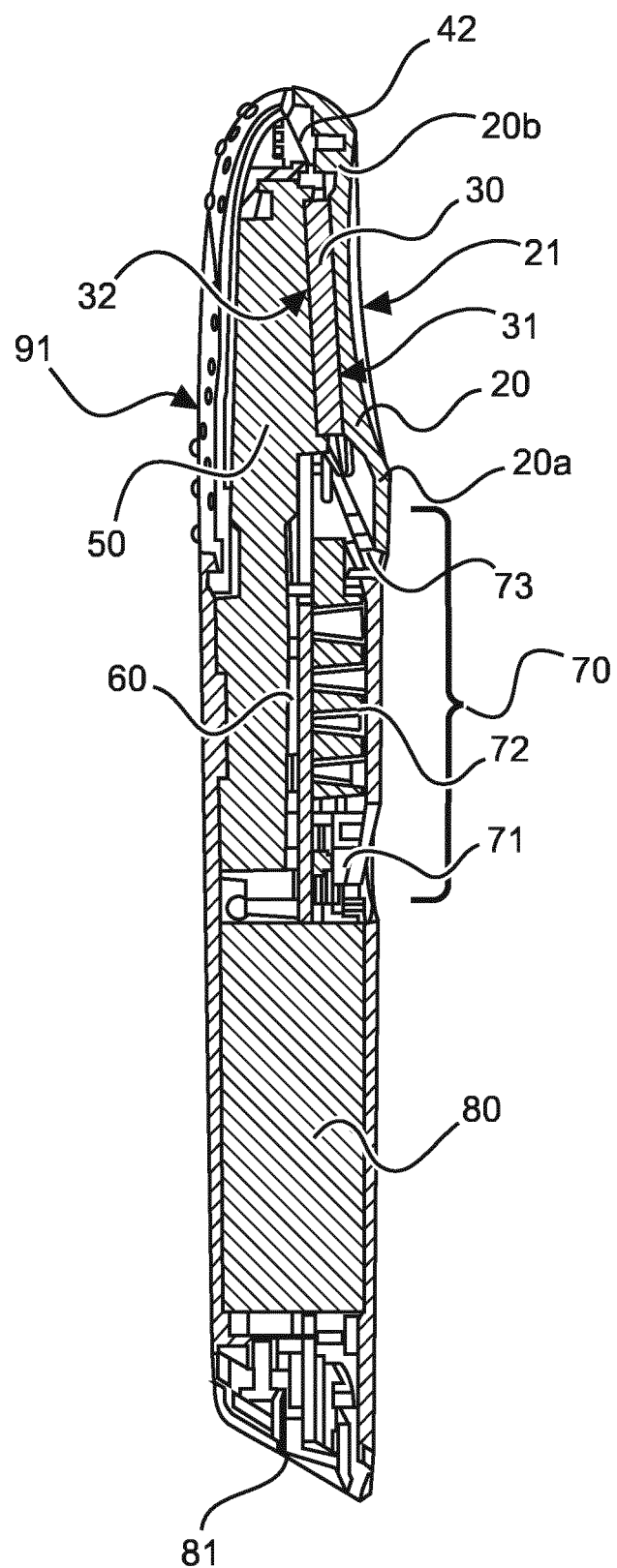
FIG. 3 shows a lateral sectional view of the device according to FIG. 1.

As can be seen particularly from FIG. 3, the Peltier element 30 extends along a center region of the skin contact component 20. The skin contact component 20 has a lower region 20a, which extends somewhat beyond the Peltier element 30 in a direction towards the lower section 11 of the device, and an upper region 20b, which extends in the opposite direction towards the upper end portion 13 of the device.

Figure 4:
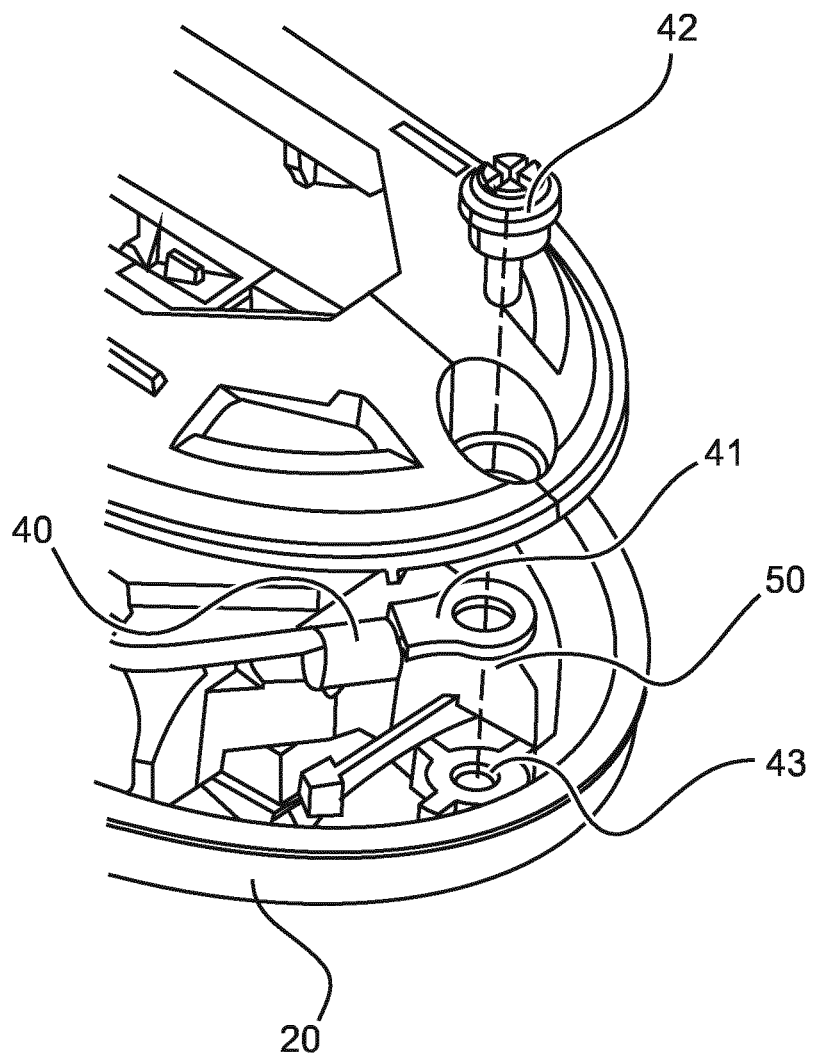
FIG. 4 shows a perspective, partially exploded view of an upper section of the device according to FIG. 1.

As can be seen in detail from FIG. 4, a temperature sensor 40, e.g. an NTC/PTC/PT100 thermocouple, is positioned in the upper region 20b of the skin contact component 20. The temperature sensor 40 is embodied as an NTC, which is connected to a wire so as to be adjacent and close to a wire lug 41. The wire lug 41 is attached to the skin contact component 20 by a screw 42 screwed into a screw hole 43. As a result, a direct heat transmission is provided from the skin contact component 20 via the wire lug 41 and the wire to the NTC, which allows accurate real-time measurement of the temperature of the skin contact component 20. The wire electrically connects the temperature sensor 40 to a temperature control circuit 60 incorporated in the device.

The Peltier element 30 is sandwiched between the skin contact component 20, which is in thermal contact with a front side 31 of the Peltier element 30, and a heat sink 50, which is in thermal contact with a back side 32 of the Peltier element 30 via a small gap filled with a thermally conductive compound. The heat sink 50 extends from the upper section 12, where it is in thermal contact with the Peltier element 30, towards the lower section 11 of the device.

Below the skin contact surface 21 in the region of the lower section 11, the temperature control circuit 60 is arranged within the housing 10. The temperature control circuit 60 includes a user interface 70 having an ON/OFF switch 71, a display 72, an illuminated signal light 73 in the form of a half circle positioned below and partially surrounding the skin contact surface 21, and a wireless signal transmission unit for transmission of signals to and from an external device. The wireless signal transmission unit may use a transmission standard like Bluetooth or any other wireless signal transmission standard.

Below the heat sink 50 and the temperature control circuit 60, a rechargeable battery 80 is incorporated in the lower section 11 of the housing 10. The rechargeable battery 80 is configured to be non-replaceable, but it is to be understood that a replaceable battery arranged in a compartment accessible via a cover or lid could be employed alternatively. The rechargeable battery 80 can be connected to an external energy source via a socket 81 arranged at the bottom end 14 of the housing, which may be configured according to a standard, e.g. a USB-socket or the like. It is to be understood that the socket 81 may serve to provide energy for recharging the battery 80 only, or it may additionally serve to transmit signals to and from the temperature control circuit 60 as an alternative signal transmission path to the wireless signal transmission unit. The Peltier element 30 is electrically connected to the battery 80 via the temperature control circuit 60.

Opposite to the skin contact surface 21, a massage pad 90 having a massage contact surface 91 is arranged in the treatment head in the upper section 12 of the housing 10. Whereas the skin contact surface 21 is formed as a curved surface with a concave shape that perfectly fits to a closed eye or serves for precision treatments of the upper or lower eyelids, the massage contact surface 91 has a slightly convex shape with multiple pressure points 92 formed as small embossments. The massage contact surface 91 has a special gliding coating to allow the massage contact surface 91 to be moved over the skin without significant friction. As a result this, a gentle massage can be applied by passive manual movement of the massage contact surface 91 across the eyelid or other skin regions.

The temperature control circuit 60 including the user interface 70 is coupled for signal transmission to the temperature sensor 40 and incorporates multiple functions for a safe and convenient use of the thermal skin treatment device. First, a temperature safety function is incorporated according to which, independent of the selection of any specific treatment program, the device is shut off if the temperature detected by the temperature sensor 40 is below 10° C. or above 45° C. In situations of a shut-off of the device, no electrical energy is supplied from the battery 80 to the Peltier element 30. The temperature control circuit 60 is further configured to control the amount of energy supplied from the battery 80 to the Peltier element 30 depending on a temperature signal transmitted by the temperature sensor 40 and depending on an operating mode selected from a plurality of operating modes stored in the temperature control circuit 60 or selected via the user interface 70. Further, the temperature control circuit 60 is adapted to change the polarity of a DC-voltage supplied by the battery 80 to the Peltier element 30 to cause the Peltier element 30 to either pump heat from the heat sink 50 to the skin contact component 20 for a heating treatment by the skin contact surface 21 or to pump heat from the skin contact component 20 to the heat sink 50 for a cooling treatment by the skin contact surface 21.

The user may switch-on the device by means of the ON/OFF button 71 of the user interface 70, and thereafter the user may select one out of three operating modes of the thermal skin treatment device by pressing the ON/OFF button shortly. The user may switch-off the device by pressing the ON/OFF button for three seconds or longer.

By pressing the ON/OFF button once in the ON-state of the device, a first operating mode, in particular a relaxing program, is selected and signalized to the user via a clear text appearing in the display 72. In this relaxing program, the temperature of the skin contact surface 21 is controlled to maintain a first predetermined temperature of 40° C. for a first duration of 4 minutes to treat both eyes of the user. To conduct this treatment, the skin contact surface 21 is heated up by the Peltier element 30. During this heating up, the signal light 73 surrounding the skin contact surface 21 blinks. When the skin contact surface 21 has reached the first predetermined temperature, the signal light 73 stops blinking and indicates a ready-to-start signal to the user by emitting in a red color. The time period of 4 minutes starts as soon as this ready-to-start signal is indicated. Alternatively, this time period may start as soon as the user brings the skin contact surface 21 into contact with the skin, which may be detected by detection of an increased heat flow from the skin contact component 21 to the skin, calculated by the temperature control circuit 60 from the energy supplied to the Peltier element 30 and the temperature detected by the temperature sensor 40. When a period of 2 minutes has elapsed, a first acoustic signal is provided by the user interface 70 signalizing to the user that the user should change the device from one eye to the other. When the total period of 4 minutes has elapsed, a second acoustic signal is provided by the user interface 70 signalizing to the user the end of the treatment according to the relaxing program.

By pressing the ON/OFF button twice in the ON-state of the device, a second operating mode, in particular a refreshing program, is selected. In this refreshing program, the temperature control circuit 60 is programmed to maintain the skin contact surface 21 at a second predetermined temperature of 19° C. for a duration of 2 minutes. As compared to the relaxing program, the polarity of the Peltier element 30 is switched and the skin contact component 20 is cooled down in closed-loop control until the skin contact surface 21 reaches the desired temperature of 19° C. When this temperature has been reached, the ready-to-start condition is signalized to the user by the signal light 73 emitting in a blue color. Like in the relaxing program, the time period of 2 minutes starts as soon as the ready-to-start condition has been reached and is signalized to the user. Alternatively, said time period may be started as soon as the skin contact surface 21 is brought into contact with the skin. When a period of 1 minute has elapsed, a first acoustic signal is provided by the user interface 70 signalizing to the user that the user should change the device from one eye to the other. When the total period of 2 minutes has elapsed, a second acoustic signal is provided by the user interface 70 signalizing to the user the end of the treatment according to the refreshing program.

By pressing the ON/OFF button three times in the ON-state of the device, a third operating mode, in particular a stimulating program, is selected. In the stimulating program, a first phase comprising a heat treatment, an intermediate phase comprising a massage treatment, and a second phase comprising a cooling treatment are activated in a timed sequence. The first phase comprising the heat treatment is conducted at the first predetermined temperature of 40° C. for a first period of 90 seconds. The ready-to-start condition is signalized to the user by the signal light 73 emitting in a red color, and the time period of 90 seconds is started at that moment by the temperature control circuit 60. The end of the first phase, after the time period of 90 seconds has elapsed, is signalized to the user by an acoustic signal. The user may then rotate the device to apply a passive manual massage by means of the massage pad 90 on the back side of the treatment head during the intermediate phase. The user may be instructed to apply the massage pad 90 by means of a suitable indication on the display 72 of the user interface 70. The duration of the intermediate phase for applying the passive manual massage is 30 seconds and starts from the end of the first phase. The end of the intermediate phase is signalized to the user by an acoustic signal.

At the start of the intermediate phase, the polarity of the energy supply to the Peltier element 30 is inverted such that the Peltier element 30 will cool down the skin contact component 20 during the intermediate phase. As a result, the skin contact surface 21 of the skin contact component 20 will cool down from the first predetermined temperature of 40° C. to the second predetermined temperature of 19° C. during the intermediate phase. At the end of the intermediate phase, an acoustic signal is provided by the user interface 70, and the user has to rotate the device back through 180° and bring the skin contact surface 21 into contact again with the skin. The second phase will start after the end of the intermediate phase. During the second phase the skin contact surface 21 is maintained at the second predetermined temperature of 19° C. for 15 seconds.

The first phase, the intermediate phase, and the second phase according to the stimulating program have to be applied in succession to one of the eyes. Thereafter, the stimulating program can be applied to the other eye. The stimulating program was found to stimulate blood flow, trigger fresh oxygen and nutrient delivery into the treated skin region in the first phase, and promote lymph drainage by the passive manual massage in the intermediate phase, and also constrict blood vessels in the eye lids in the second phase, causing dark circles to become less visible or reducing the perceived visibility of such dark circles.

The user may connect an external device, like a smartphone, a computer or any other electronic device serving as a base station, by the wireless user interface, and may thus use the external device to select and program individual settings or operating modes. This enables the three operating modes, i.e. the relaxing program, the refreshing program and the stimulating program, to be adapted according to personal preferences of the user, and such personal settings may be stored in the temperature control circuit 60 for future use. Further, the user may program individual treatment programs, like multiple-phase treatments comprising an alternation of heating treatments, cooling treatments and massage treatments according to personal preferences. These individual treatment programs may also be stored in the temperature control circuit 60, such as to allow the user to select such individual treatment programs for future use. Said personal settings may include the temperature levels, the durations of the time periods during which the temperature levels are maintained, the type of signalizing via the user interface the start and the end of the treatment programs and/or the phases of the treatment programs. In all cases, a personal selection of the temperature levels is only possible within the safe and effective limits provided by the ranges for the first and second predetermined temperatures according to the present invention.

The device may further include a skin sensor 95 incorporated in the massage pad 90 or in the skin contact surface 21 to detect certain properties of the skin, e.g. the electrical resistivity of the skin, the electrical capacity of the skin, the temperature of the skin and/or the humidity of the skin. The signal of the skin sensor 95 may be transmitted to the temperature control circuit 60 or to an external device. The temperature control circuit 60 may control the user interface 70 to display information about the skin to the user. The temperature control circuit 60 may adapt the temperature and/or duration settings of the treatment programs to better conform to the condition of the user's skin. For example, the skin sensor 95 may detect that the skin temperature is significantly below normal human body temperature, and in such a condition the temperature control circuit 60 may modify the program settings to increase the duration of heating treatment and to reduce the duration of cooling treatment to better fit the condition of the user's skin.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A thermal skin treatment device, comprising:
a skin contact component with a skin contact surface,
a thermal energy component in thermal contact with the skin contact component,
a temperature control circuit electrically connected to the thermal energy component, said temperature control circuit comprising a user interface,
an energy source electrically connected to said thermal energy component for energy supply,
wherein said temperature control circuit is adapted to control an amount of energy supplied from said energy source to said thermal energy component such that
an upper predetermined temperature is maintained at the skin contact surface for a first duration, wherein said upper predetermined temperature is in a range of 40° C.+/−2° C., and
a lower predetermined temperature is maintained at the skin contact surface for a second duration, wherein said lower predetermined temperature is in a range of 19° C.+/−2° C.,
wherein
said temperature control circuit is configured to control the amount of energy supplied from said energy source to said thermal energy component according to a fluctuating mode such that the upper predetermined temperature periodically fluctuates within said range of 40° C.+/−2° C. to intensify treatment effects during the first duration, and
said temperature control circuit is further configured to control the amount of energy supplied from said energy source to said thermal energy component according to the fluctuating mode such that the lower predetermined temperature periodically fluctuates within said range of 19° C.+/−2° C. to intensify treatment effects during the second duration,
wherein said temperature control circuit is adapted to selectively maintain for a predetermined duration, during operation according to one or more phases of a given operating mode or a given thermal skin treatment program, only said upper predetermined temperature or said lower predetermined temperature at the skin contact surface.

2. The thermal skin treatment device according to claim 1, wherein said user interface is adapted for selection between at least two different operating modes selected from:
a first operating mode, wherein the upper predetermined temperature is maintained at the skin contact surface and wherein the first duration is in a range from 60 to 240 seconds;
a second operating mode, wherein the lower predetermined temperature is maintained at the skin contact surface and wherein the second duration is in a range from 30 to 90 seconds; and
a third operating mode, wherein alternately the upper predetermined temperature is maintained at the skin contact surface, with the first duration being in a range from 60 to 150 seconds, and the lower predetermined temperature is maintained at the skin contact surface, with the second duration being in a range from 5 to 30 seconds.

3. The thermal skin treatment device according to claim 1, wherein said user interface is adapted for selection of a thermal massage operating mode wherein:
in a first phase the skin contact surface is maintained at the upper predetermined temperature, wherein the first duration is from 60 to 150 seconds;
in a second phase, after the first phase, the skin contact surface is maintained at the lower temperature, wherein the second duration is from 5 to 30 seconds; and
in an intermediate phase, starting after the first phase has ended and before the second phase has started, the user is instructed to apply a massage to the skin for a duration from 15 to 60 seconds.

4. The thermal skin treatment device according to claim 1, wherein at least one of the first and second durations is programmable via the user interface.

5. The thermal skin treatment device according to claim 1, wherein the temperature control circuit is adapted to receive a user input via said user interface, said user input representing a temperature selection of a user, wherein said temperature control unit is adapted to adjust said upper predetermined temperature within the range of 40° C.+/−2° C. to a higher or a lower value depending on the user input and/or to adjust said lower predetermined temperature within the range of 19° C.+/−2° C. to a higher or a lower value depending on the user input.

6. The thermal skin treatment device according to claim 1, further comprising:
a temperature sensor coupled to the temperature control circuit for transmission of a temperature signal corresponding to a temperature detected by the temperature sensor;
wherein said temperature sensor is in thermal contact with the skin contact component.

7. The thermal skin treatment device according to claim 6, wherein the temperature control circuit is adapted to control the amount of energy supplied from the energy source to the thermal energy component depending on the temperature signal transmitted by the temperature sensor.

8. The thermal skin treatment device according to claim 1, further comprising a heat sink in thermal contact with the thermal energy component, wherein a ratio of a heat capacity of the skin contact component to a heat capacity of the heat sink is in a range from 1:2 to 1:10.

9. The thermal skin treatment device according to claim 8, wherein the ratio of the heat capacity of the skin contact component to the heat capacity of the heat sink is in a range from 1:2.5 to 1:5.

10. The thermal skin treatment device according to claim 1, wherein the skin contact surface has a concave shape with a curvature having an average radius along said surface in a range from 50 mm to 200 mm.

11. The thermal skin treatment device according to claim 1, wherein the skin contact surface is arranged at an end portion of the thermal skin treatment device, and wherein a massage contact surface having a non-smooth surface is arranged at said end portion.

12. The thermal skin treatment device according to claim 1, wherein the user interface comprises signaling means for signaling to the user at least one parameter related to a temperature or a duration controlled by the temperature control circuit.

13. The thermal skin treatment device according to claim 1, wherein said skin contact component, said thermal energy component, said temperature control circuit, and said energy source are integrally mounted in a handheld device, said energy source being embodied as a rechargeable or replaceable battery.

14. The thermal skin treatment device according to claim 1, further comprising a skin sensor adapted to measure an electrical resistivity of the skin, an electrical capacity of the skin, a temperature of the skin, a humidity of the skin, or a combination thereof,
wherein said skin sensor is coupled to said temperature control circuit for signal transmission, and
wherein said temperature control circuit is adapted to display a skin condition on said user interface and/or to control said upper or lower predetermined temperature or said first or second duration, depending on a signal transmitted by the skin sensor.

15. The thermal skin treatment device according to claim 1, wherein
the upper predetermined temperature fluctuates by up to 2° C. within the range of 40° C.+/−2° C., and/or
the lower predetermined temperature fluctuates by up to 2° C. within the range of 19° C.+/−2° C.

16. A method for non-therapeutic treatment of a human eye region by means of a thermal skin treatment device, having:
a skin contact component with a skin contact surface,
a thermal energy component in thermal contact with the skin contact component,
a temperature control circuit electrically connected to the thermal energy component, said temperature control circuit comprising a user interface, and
an energy source electrically connected to said thermal energy component for energy supply;
the method comprising:
controlling, by means of said temperature control circuit, an amount of energy supplied from said energy source to said thermal energy component such that
an upper predetermined temperature is maintained at the skin contact surface for a first duration, and
a lower predetermined temperature is maintained at the skin contact surface for a second duration,
wherein said upper predetermined temperature is in a range of 40° C.+/−2° C., and
wherein said lower predetermined temperature is in a range of 19° C.+/−2° C., and
selectively maintaining for a predetermined duration, by means of said temperature control circuit during operation according to one or more phases of a given operating mode or a given thermal skin treatment program, only said upper predetermined temperature or said lower predetermined temperature at the skin contact surface,
wherein
said temperature control circuit is configured to control the amount of energy supplied from said energy source to said thermal energy component according to a fluctuating mode such that the upper predetermined temperature periodically fluctuates within said range of 40° C.+/−2° C. to intensify treatment effects during the first duration, and
said temperature control circuit is further configured to control the amount of energy supplied from said energy source to said thermal energy component according to the fluctuating mode such that the lower predetermined temperature periodically fluctuates within said range of 19° C.+/−2° C. to intensify treatment effects during the second duration.

17. A thermal skin treatment device, comprising:
a thermal energy component for directing heat toward a skin contact surface; and
a temperature control circuit electrically connected to the thermal energy component, said temperature control circuit comprising a user interface, wherein
said temperature control circuit is configured to control an amount of energy supplied from an energy source to said thermal energy component according to a fluctuating mode such that an upper predetermined temperature periodically fluctuates within a range of 40° C.+/−2° C. to intensify treatment effects during a first duration, and
said temperature control circuit is adapted to control the amount of energy supplied from said energy source to said thermal energy component according to the fluctuating mode such that a lower predetermined temperature periodically fluctuates within a range of 19° C.+/−2° C. to intensify treatment effects during a second duration, and
wherein said temperature control circuit is further adapted to selectively maintain for a predetermined duration, during operation according to one or more phases of a given operating mode or a given thermal skin treatment program, only said upper predetermined temperature or said lower predetermined temperature at the skin contact surface.

18. The thermal skin treatment device according to claim 17, wherein
the upper predetermined temperature fluctuates by up to 2° C. within the range of 40° C.+/−2° C. at a given frequency during the first duration, and
the lower predetermined temperature fluctuates by up to 2° C. within the range of 19° C.+/−2° C. at the given frequency during the second duration.

19. The thermal skin treatment device according to claim 17, further comprising a skin contact component with a skin contact surface, wherein
the skin contact component is in thermal contact with the thermal energy component, and
the skin contact surface has a concave shape with a curvature having an average radius along said surface in a range from 50 mm to 200 mm.

20. The thermal skin treatment device according to claim 17, further comprising a power source, wherein the skin contact component, the thermal energy component, the temperature control circuit, and the energy source are integrally mounted in a handheld device.

* * * * *